US009293670B2

(12) United States Patent
Toita et al.

(10) Patent No.: US 9,293,670 B2
(45) Date of Patent: Mar. 22, 2016

(54) ULTRAVIOLET LIGHT-EMITTING DEVICES AND METHODS

(71) Applicants: Masato Toita, Tokyo (JP); Jianfeng Chen, Clifton Park, NY (US); Yuxin Li, Green Island, NY (US); Yuting Wang, Tokyo (JP); Hironori Ishii, Tokyo (JP); Ken Kitamura, Tokyo (JP)

(72) Inventors: Masato Toita, Tokyo (JP); Jianfeng Chen, Clifton Park, NY (US); Yuxin Li, Green Island, NY (US); Yuting Wang, Tokyo (JP); Hironori Ishii, Tokyo (JP); Ken Kitamura, Tokyo (JP)

(73) Assignee: Crystal IS, Inc., Green Island, NY (US)

( * ) Notice: Subject to any disclaimer, the term of this patent is extended or adjusted under 35 U.S.C. 154(b) by 0 days.

(21) Appl. No.: 14/679,655

(22) Filed: Apr. 6, 2015

(65) Prior Publication Data
US 2015/0287894 A1    Oct. 8, 2015

Related U.S. Application Data

(60) Provisional application No. 61/976,064, filed on Apr. 7, 2014.

(51) Int. Cl.
| | | |
|---|---|---|
| *H01L 23/48* | (2006.01) | |
| *H01L 23/52* | (2006.01) | |
| *H01L 29/40* | (2006.01) | |
| *H01L 33/58* | (2010.01) | |
| *H01L 33/56* | (2010.01) | |
| *H01L 33/48* | (2010.01) | |
| *H01L 33/62* | (2010.01) | |

(52) U.S. Cl.
CPC .............. *H01L 33/58* (2013.01); *H01L 33/486* (2013.01); *H01L 33/56* (2013.01); *H01L 33/62* (2013.01)

(58) Field of Classification Search
CPC .................. H01L 21/02348; H01L 21/02351; H01L 21/02178; H01L 21/56; H01L 21/565; H01L 23/4951; H01L 23/53233; H01L 51/53219; H01L 27/0814; H01L 29/6603; H01L 51/0034; H01L 51/4226; H01L 51/5296
USPC ............ 257/749, 79, 98, 104, 290, 292, 293, 257/294, 431, 603, 659, 762, 787, 791, 257/E21.006, E21.007, E21.053, E21.027, 257/E21.077, E21.134, E21.264, E21.266, 257/E21.267, E21.32, E21.329, E21.347, 257/E21.352, E21.502, E21.499
See application file for complete search history.

(56) References Cited

U.S. PATENT DOCUMENTS

| | | | | |
|---|---|---|---|---|
| 8,294,160 B2* | 10/2012 | Suehiro | ................... | H01L 33/56 257/79 |
| 8,884,326 B2* | 11/2014 | Tischler | ................... | H01L 33/50 257/98 |
| 8,896,010 B2* | 11/2014 | Tischler | ................... | H01L 24/96 257/98 |
| 8,962,359 B2* | 2/2015 | Schowalter | ............. | H01L 33/22 438/27 |

(Continued)

FOREIGN PATENT DOCUMENTS

JP        2006-261688 A       9/2006

OTHER PUBLICATIONS

International Search Report and Written Opinion issued in a corresponding International Application No. PCT/US2015/024526 dated Jul. 14, 2015.

*Primary Examiner* — David Nhu
(74) *Attorney, Agent, or Firm* — Morgan, Lewis & Bockius LLP

(57) ABSTRACT

In various embodiments, an illumination device features an ultraviolet (UV) light-emitting device at least partially surrounded by an encapsulant. A barrier layer is disposed between the light-emitting device and the encapsulant and is configured to substantially prevent UV light emitted by the light-emitting device from entering the encapsulant.

30 Claims, 5 Drawing Sheets

(56) References Cited

U.S. PATENT DOCUMENTS

| | | |
|---|---|---|
| 2005/0072981 A1 | 4/2005 | Suenaga |
| 2011/0104834 A1 | 5/2011 | Suehiro et al. |
| 2011/0180833 A1 | 7/2011 | Jang et al. |
| 2012/0313130 A1 | 12/2012 | Ramer et al. |

* cited by examiner

ULTRAVIOLET LIGHT-EMITTING DEVICES AND METHODS

RELATED APPLICATION

This application claims the benefit of and priority to U.S. Provisional Patent Application No. 61/976,064, filed Apr. 7, 2014, the entire disclosure of which is hereby incorporated herein by reference.

TECHNICAL FIELD

In various embodiments, the present invention relates to light emitters emitting ultraviolet (UV) radiation.

BACKGROUND

Light-emitting diodes (LEDs) are increasingly utilized in a variety of different lighting applications due to their lower energy consumption, longer lifetime, high physical robustness, small size, and fast switching times. FIG. 1 depicts a conventional LED package 100, in which an LED chip 105 is electrically and physically connected to a submount 110 on a surface-mount device (SMD) package 115. Wires 120 electrically connect submount contacts to contact pads 125 on the SMD package 115, and a plastic lens 130 is placed over the LED chip 105 to focus the light therefrom. As shown, a transparent liquid- or gel-based "glob top" encapsulant 135 is then disposed over all of the components within the SMD package 115 and cured to form a semi-rigid protective coating that is also transparent to light emitted by the LED chip 105. The encapsulant 135 typically has a lens-like shape to facilitate light emission from the packaged LED chip 105. LED package 100 also may feature one or more electrical contacts 140 that electrically connect the LED chip 105 to the submount 110, as well as an underfill 145. As shown, the underfill 145 may be disposed between the LED chip 105 and the submount 110 and provide mechanical support to the LED chip between the electrical contacts 140.

UV LEDs have shown great promise for applications such as medical therapy, sensors and instrumentation, and fluid sterilization. Unfortunately, the above-described conventional packaging is frequently unsuitable for UV LEDs, which may emit light having wavelengths less than 320 nm, less than 265 nm, or even less than 200 nm. As shown in FIG. 1, when the LED chip is a UV LED, the highly energetic UV light leads to deterioration and even formation of cracks 150 within the transparent encapsulant. Such cracking may lead to distortions or breaks in the bonding wires 120 or failure of the LED package 100 due to moisture introduced from the outside environment along the cracks 150. In addition, the UV radiation from UV LEDs can cause deterioration and even failure of the plastic lenses 130 that are typically utilized atop other (e.g., visible-light-emitting) LEDs. In view of these issues, there is a need for improved packaging schemes for UV LEDs that enable high reliability, mechanical robustness, and long lifetime for the packaged devices.

SUMMARY

In accordance with various embodiments of the present invention, high-reliability packages for UV LED chips include rigid lenses resistant to UV damage or deterioration in combination with a barrier layer between light-emitting portions of the LED chip and any transparent encapsulant utilized to encase the LED chip within the package. The barrier layer substantially prevents transmission of UV light through the majority of such encapsulant, thereby preventing deterioration and cracking (or other mechanical failure) thereof. In various embodiments of the invention, the barrier layer includes or consists essentially of a portion of the encapsulant itself that is adjacent to the LED chip and opaque to the UV light emitted by the LED chip. (In such embodiments, the remaining portion of the encapsulant farther away from the LED chip may also be UV-opaque or transparent, as this more distant encapsulant will typically not transmit the emitted UV light.) As utilized herein, an "opaque" material substantially does not transmit light of a particular wavelength or wavelength range (e.g., UV light), and instead is reflective and/or strongly absorptive (e.g., over a small thickness) to light of the particular wavelength or wavelength range. In other embodiments of the invention, the barrier layer includes or consists essentially of a solid opaque shield disposed between the LED chip and the encapsulant, which may itself therefore be transparent or opaque to UV light. For example, the shield may be composed of a metal that is substantially reflective to UV light such as aluminum. In this manner, embodiments of the invention include packaged UV LEDs having long lifetimes, high output power, and high reliability.

Moreover, various embodiments of the present invention ameliorate or prevent output degradation and/or lens detachment in packaged UV LEDs. In various embodiments, a force is applied between the LED chip and a lens (e.g., a rigid lens) thereover in order to maintain contact therebetween during thermal curing of the encapsulant material and/or during UV emission (e.g., during operation and/or during burn-in processes in manufacturing). For example, the force may be a downward force applied to the lens toward the LED chip, an upward force applied to the LED chip toward the lens, or a combination of both. The force may advantageously suppress or substantially prevent formation of bubbles within and/or at a thin layer of an interface material that is disposed between the LED chip and the lens. Such bubbles may be due, at least in part, to, e.g., gas generated by decomposition of the interface material during curing and/or during UV emission while the LED is in operation. For example, application of heat to an interface material including or consisting essentially of silicone may result in the formation of bubbles of formaldehyde gas. Furthermore, while the LED is in operation, the emitted UV light may induce a photochemical reaction that takes place in the interface material, and this reaction may result in decomposition of silicone that may result in the formation of bubbles within the interface material. The presence of the bubbles may deleteriously impact the UV transparency of the interface material, and, if large enough, may result in at least partial detachment of the lens from the LED chip. The force, which may have a magnitude of, e.g., between approximately 0.05 Newtons and approximately 10 Newtons, may be applied by a portion of the encapsulant itself that vertically overlaps the lens. When the encapsulant is cured, by e.g., application of heat, at least a portion of the encapsulant may thermally contract (due to, e.g., heat-induced volumetric shrinkage) and thereby apply the bubble-preventing force to the lens. For example, the encapsulant may include, consist essentially of, or consist of a "heat-contractive material," i.e., a material that experiences volumetric contraction upon application of heat. The volumetric contraction typically remains, at least in part, after heating is complete (i.e., the original volume of the heat-contractile material is not recovered, at least not entirely, after the heating is finished). The heat-contractive material may include, consist essentially of, or consist of, for example, a resin, e.g., a resin of polytetrafluoroethylene (PTFE), polyetheretherketone (PEEK), a fluoropolymer such as a perfluoroalkoxy alkane (PFA), and/ or epoxy. In various embodiments, epoxy resin may be utilized for its advantageous moisture-blocking properties. At least in part because heat-contractive materials in accordance with embodiments of the present invention are elastic, and retain at least a portion of their elasticity after volumetric contraction, at least a portion of the force applied thereby during curing is retained even after curing (and in the absence of applied heat). The force may continue to be applied by the heat-contractive material for a period of at least 10,000 hours, or even at least 50,000 hours, and/or for a time period substantially equal to or exceeding the expected lifetime of one or more other components (e.g., the LED chip) of packaged UV LEDs in accordance with embodiments of the present invention.

In an aspect, embodiments of the invention feature an illumination device that includes or consists essentially of a light-emitting device, a package, an encapsulant, and a barrier layer. The light-emitting device is configured to emit ultraviolet (UV) light and may have at least two spaced-apart contacts. At least a portion of the package may be disposed beneath the light-emitting device. The contacts of the light-emitting device are electrically connected to the package. The light-emitting device may be mechanically attached to a portion of the package. The encapsulant may be disposed on the package. The encapsulant at least partially surrounds the light-emitting device. The barrier layer is disposed between the light-emitting device and the encapsulant. The barrier layer is configured (e.g., sized and/or shaped and/or positioned) to substantially prevent UV light emitted by the light-emitting device from entering the encapsulant.

Embodiments of the invention may include one or more of the following in any of a variety of combinations. The barrier layer may include, consist essentially of, or consist of a second encapsulant disposed adjacent to the light-emitting device. The second encapsulant may be opaque to UV light emitted by the light-emitting device. The encapsulant may be substantially transparent to UV light emitted by the light-emitting device. The encapsulant may be opaque to UV light emitted by the light-emitting device. The encapsulant and the second encapsulant may include, consist essentially of, or consist of the same material. A penetration length of UV light (e.g., the UV light emitted by the light-emitting device and/or UV light having a wavelength range partially or fully overlapping with that of the UV light emitted by the light-emitting device) within the second encapsulant may be less than 25 μm, or even less than 10 μm. A penetration length of UV light within the encapsulant may be 100 μm or more (and may even be longer than a dimension, e.g., width, radius, etc., of the encapsulant).

The barrier layer may include, consist essentially of, or consist of a material reflective to UV light emitted by the light-emitting device. The barrier layer may include, consist essentially of, or consist of aluminum. At least a portion of the encapsulant may be substantially transparent to UV light emitted by the light-emitting device. At least a portion of the encapsulant may be substantially opaque to UV light emitted by the light-emitting device. The UV light emitted by the light-emitting device may have a wavelength of 265 nm or less, or even 200 nm or less (and may have a wavelength of 10 nm or more). The package may include or consist essentially of a submount and a surface-mount-device (SMD) package. The contacts of the light-emitting device may be electrically and mechanically connected to the submount. The submount may be disposed above the SMD package and/or may be electrically connected to the SMD package. The submount may be electrically connected to the SMD package via one or more wire bonds.

A rigid inorganic lens may be disposed above the light-emitting device and may at least partially protrude from the encapsulant. The lens may include, consist essentially of, or consist of quartz, fused silica, and/or sapphire. A top surface of the encapsulant (e.g., the top surface of the encapsulant adjoining and/or in contact with the lens) may be disposed above a bottom surface of the lens by at least 0.05 mm. At least a portion of the encapsulant may apply a downward force on the lens toward the light-emitting device. The magnitude of the downward force may be greater than 0.1 N. A thin interface material (e.g., a gel, resin, cured or at least partially uncured polymer, or liquid) may be disposed between the lens and the light-emitting device. The interface material may have a thickness less than 5 μm. The interface material may include, consist essentially of, or consist of silicone (e.g., a silicon resin). At least a portion of the encapsulant may apply a downward force on the lens and/or on the interface material toward the light-emitting device. The magnitude of the downward force may be greater than 0.1 N. The light-emitting device may include, consist essentially of, or consist of a light-emitting diode (e.g., a bare-die light-emitting diode or light-emitting diode chip) or a laser (e.g., a bare-die laser or laser chip). The encapsulant may include, consist essentially of, or consist of a heat-contractive material. The encapsulant may include, consist essentially of, or consist of polytetrafluoroethylene, polyetheretherketone, a fluoropolymer such as a perfluoroalkoxy alkane, and/or epoxy (e.g., a resin of one or more of these materials). The encapsulant may include, consist essentially of, or consist of epoxy (e.g., epoxy resin).

In another aspect, embodiments of the invention feature a method for forming an illumination device. An apparatus is provided. The apparatus includes, consists essentially of, or consists of a light-emitting device configured to emit ultraviolet (UV) light, a rigid inorganic lens disposed over the light-emitting device, an interface material disposed between the light-emitting device and the lens, and an encapsulant. The encapsulant at least partially surrounds the light-emitting device and contacts at least a portion of the lens. The lens may at least partially protrude from the encapsulant. The encapsulant is partially or substantially fully cured. While the encapsulant is being partially or substantially fully cured, a downward force is applied on the lens toward the light-emitting device (equivalently, the light-emitting device may be forced upward toward the lens and/or the light-emitting device and lens may be forced toward each other). The downward force (i) substantially prevents partial or full detachment of the lens from the light-emitting device, and/or (ii) substantially suppresses formation of bubbles between the light-emitting device and the lens (and/or substantially prevents bubbles from remaining between the light-emitting device and the lens).

Embodiments of the invention may include one or more of the following in any of a variety of combinations. The apparatus may include a barrier layer configured to substantially prevent UV light emitted by the light-emitting device from entering the encapsulant. The barrier layer may be disposed between the light-emitting device and the encapsulant. The barrier layer may include, consist essentially of, or consist of a second encapsulant disposed adjacent to the light-emitting device (and may be in contact with the light-emitting device). The second encapsulant may be opaque to UV light emitted by the light-emitting device. The encapsulant may be substantially transparent to UV light emitted by the light-emitting device. The encapsulant may be opaque to UV light emitted by the light-emitting device. The encapsulant and the second encapsulant may include, consist essentially of, or consist of the same material. A penetration length of UV light within the second encapsulant is less than or equal to 25 µm, or even less than or equal to 10 µm. A penetration length of UV light within the encapsulant may be 100 µm or more.

The barrier layer may include, consist essentially of, or consist of a material reflective to UV light emitted by the light-emitting device. The barrier layer may include, consist essentially of, or consist of aluminum. At least a portion of the encapsulant may be substantially transparent to UV light emitted by the light-emitting device. At least a portion of the encapsulant may be opaque to UV light emitted by the light-emitting device. The UV light emitted by the light-emitting device may have a wavelength of 265 nm or less, or even 200 nm or less. The lens may include, consist essentially of, or consist of quartz, fused silica, and/or sapphire. A top surface of the encapsulant may be disposed above a bottom surface of the lens by at least 0.05 mm. The magnitude of the downward force may be greater than 0.1 N. The downward force may be applied by contraction of at least a portion of the encapsulant during partial curing or substantially full curing of the encapsulant. The interface material may have a thickness less than 5 µm. The interface material may include, consist essentially of, or consist of silicone (e.g., silicone resin). The light-emitting device may include, consist essentially of, or consist of a light-emitting diode (e.g., a bare-die light-emitting diode or light-emitting diode chip) or a laser (e.g., a bare-die laser or laser chip). The encapsulant may include, consist essentially of, or consist of a heat-contractive material. The encapsulant may include, consist essentially of, or consist of polytetrafluoroethylene, polyetheretherketone, a fluoropolymer such as a perfluoroalkoxy alkane, and/or epoxy (e.g., a resin of one or more of these materials). The encapsulant may include, consist essentially of, or consist of epoxy (e.g., epoxy resin). The downward force may substantially suppress formation of bubbles arising from decomposition of the interface material (and/or substantially prevent such bubbles from remaining between the light-emitting device and the lens).

In another aspect, embodiments of the invention feature a method for emitting ultraviolet (UV) light using a light-emitting device at least partially surrounded by an encapsulant. Power is supplied to the light-emitting device, thereby causing the light-emitting device to emit UV light. While power is being supplied to the light-emitting device (and the light-emitting device is emitting UV light), UV light emitted by the light-emitting device is substantially prevented from entering (and/or deteriorating, and/or cracking, and/or penetrating more than 25 µm into, or even penetrating more than 10 µm into) the encapsulant.

Embodiments of the invention may include one or more of the following in any of a variety of combinations. The penetration length of UV light within the encapsulant may be 100 µm or more. UV light emitted by the light-emitting device may be prevented from entering the encapsulant at least in part by a barrier layer disposed between the light-emitting device and the encapsulant. The barrier layer may include, consist essentially of, or consist of a second encapsulant disposed adjacent to the light-emitting device. The second encapsulant may be opaque to UV light emitted by the light-emitting device. The encapsulant may be substantially transparent to UV light emitted by the light-emitting device. The encapsulant may be substantially opaque to UV light emitted by the light-emitting device. The encapsulant and the second encapsulant may include, consist essentially of, or consist of the same material. A penetration length of UV light within the second encapsulant is less than or equal to 25 µm, or even less than or equal to 10 µm.

The barrier layer may include, consist essentially of, or consist of a material reflective to UV light emitted by the light-emitting device. The barrier layer may include, consist essentially of, or consist of aluminum. At least a portion of the encapsulant may be substantially transparent to UV light emitted by the light-emitting device. At least a portion of the encapsulant may be opaque to UV light emitted by the light-emitting device. The UV light emitted by the light-emitting device may have a wavelength of 265 nm or less, or even 200 nm or less.

A rigid inorganic lens may be disposed above the light-emitting device and at least partially protrude from the encapsulant. The lens may include, consist essentially of, or consist of quartz, fused silica, and/or sapphire. A top surface of the encapsulant may be disposed above a bottom surface of the lens by at least 0.05 mm. A force (e.g., a downward force) may be applied on the lens toward the light-emitting device (and/or a force may be applied on the light-emitting device toward the lens, and/or force may be applied on the lens and the light-emitting device toward each other). At least a portion of the force may be applied by the encapsulant. The magnitude of the force may be greater than 0.1 N. An interface material may be disposed between the lens and the light-emitting device. The interface material may have a thickness less than 5 µm. The interface material may include, consist essentially of, or consist of silicone. At least a portion of the encapsulant may apply a downward force on the lens toward the light-emitting device. The magnitude of the downward force may be greater than 0.1 N. The light-emitting device may include, consist essentially of, or consist of a light-emitting diode (e.g., a bare-die light-emitting diode or light-emitting diode chip) or a laser (e.g., a bare-die laser or laser chip). The encapsulant may include, consist essentially of, or consist of a heat-contractive material. The encapsulant may include, consist essentially of, or consist of polytetrafluoroethylene, polyetheretherketone, a fluoropolymer such as a perfluoroalkoxy alkane, and/or epoxy (e.g., a resin of one or more of these materials). The encapsulant may include, consist essentially of, or consist of epoxy (e.g., epoxy resin).

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "substantially" and "approximately" mean ±10%, and in some embodiments, ±5%. The term "consists essentially of" means excluding other materials that contribute to function, unless otherwise defined herein. Nonetheless, such other materials may be present, collectively or individually, in trace amounts. Herein, the terms "radiation" and "light" are utilized interchangeably unless otherwise indicated.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
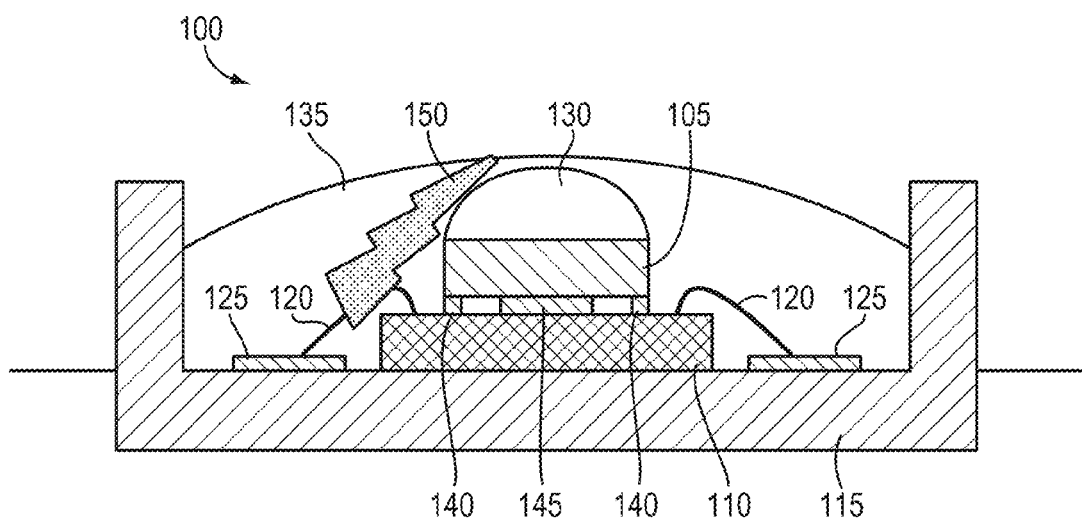
FIG. 1 is a cross-sectional schematic of a conventional packaged LED.
Figure 2:
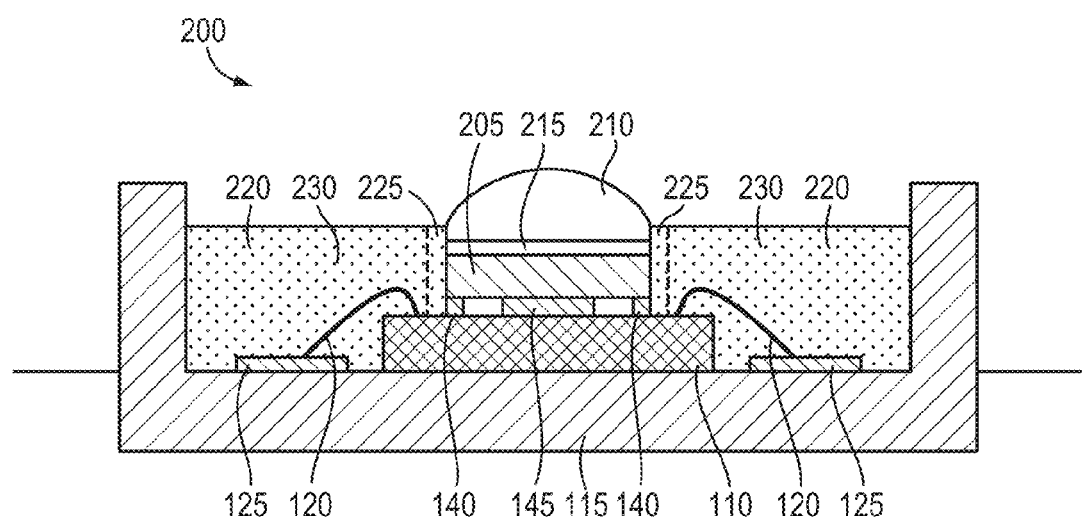
FIG. 2 is a cross-sectional schematic of a packaged UV LED in accordance with various embodiments of the invention.

FIG. 2 is a cross-sectional view of a packaged UV LED 200 in accordance with various embodiments of the present invention. As shown, a UV LED chip 205 is electrically and mechanically connected to the submount 110, which is itself electrically connected via one or more wire bonds 120 to the SMD package 115. The submount 110 may include or consist essentially of, e.g., a ceramic material, and may have electrically conductive pads thereon to which wires 120 and electrical contacts 140 are electrically connected. The submount 110 may be thermally conductive in order to conduct heat away from UV LED chip 205 during operation. For example, submount 110 may include or consist essentially of aluminum nitride and/or aluminum oxide. In other embodiments, the submount 110 may include or consist essentially of one or more metals, e.g., copper, or one or more semiconductor materials, e.g., silicon. In various embodiments, one or more of the inner surfaces (i.e., the surfaces facing the UV LED chip 205) of the SMD package 115 are reflective to the UV light emitted by UV LED chip 205. The SMD package 115 may include, consist essentially of, or consist of, for example, one or more plastics such as polyphthalamide (PPA) and/or one or more ceramics such as aluminum nitride or alumina. In various embodiments, one or more surfaces (or even the entirety) of the SMD package 115 may be coated with a material reflective to UV light (e.g., aluminum). For example, the inner surface of SMD package 115, i.e., the surface facing the UV LED chip 205, may be coated with aluminum formed by, e.g., non-electrolytic plating.

The UV LED chip 205 may include an AlN substrate and, thereover, one or more quantum wells and/or strained layers including or consisting essentially of AlN, GaN, InN, or any binary or tertiary alloy thereof. In various embodiments, UV LED 205 includes a substrate and/or device structure resembling those detailed in U.S. Pat. No. 7,638,346, filed on Aug. 14, 2006, U.S. Pat. No. 8,080,833, filed on Apr. 21, 2010, and/or U.S. Patent Application Publication No. 2014/0264263, filed on Mar. 13, 2014, the entire disclosure of each of which is incorporated by reference herein.

Rather than a conventional plastic lens, an inorganic (and typically rigid) lens 210 (e.g., a lens including or consisting essentially of fused silica, quartz, and/or sapphire) is coupled directly to the UV LED chip 205 via a thin layer of an interface material 215 (e.g., an organic, UV-resistant encapsulant compound that may include or consist essentially of a silicone resin). An exemplary interface material 215 that may be utilized in embodiments of the present invention is Deep UV-200 available from Schott North America, Inc. of Elmsford, N.Y. As utilized herein, an "interface material" is a material that substantially fills any air gaps between, for example, a light-emitting device and a lens. In some embodiments, the interface material has an index of refraction substantially matched to at least one of the components joined thereby, or an index of refraction that lies between those of the components joined by the interface material. Interface materials may be liquid or gelatinous when applied, but may be curable to form substantially solid layers. Interface materials may or may not be intrinsically adhesive. In various embodiments of the present invention, the thin layer of interface material 215 is preferably quite thin (e.g., less than 5 µm thick, or even 3 µm thick or less) to minimize or prevent deterioration thereof by the energetic UV radiation from the UV LED chip 205. The thickness of the interface material 215 may be at least 1 µm. The inorganic lens 210 is itself resistant to UV-light-induced deterioration. This approach, which is also detailed in U.S. patent application Ser. No. 13/553,093, filed on Jul. 19, 2012 ("the '093 application," the entire disclosure of which is incorporated by reference herein), increases the critical angle of total internal reflection through the top surface of the UV LED chip 205, which significantly improves photon-extraction efficiency for the packaged UV LED 200.

In addition, an encapsulant 220 encases the UV LED chip 205 within the SMD package 115; as shown, the encapsulant 220 may not entirely cover (and may not even contact) the rigid inorganic lens 210. At least a portion of the encapsulant 220 (e.g., the portion of the encapsulant 220 bordering and/or in contact with the UV LED chip 205 and/or the lens 210) may be substantially opaque to the UV light emitted by the UV LED chip 205; thus, any UV light emitted into the encapsulant 220 is confined in an extremely shallow depth of the encapsulant 220, and the energetic UV light does not interact with most of the encapsulant 220. Thus, the encapsulant 220 is more resistant to deterioration and cracking, and the packaged UV LED 200 exhibits greater reliability.

In preferred embodiments, the penetration length of UV light (e.g., light having a wavelength of 265 nm or less, or even 200 nm or less) of the encapsulant 220, i.e., the distance within the encapsulant 220 during which the intensity of the light decreases to 10% or less of the incident value, is less than 25 µm, or even less than 10 µm. (In contrast, conventional encapsulants having penetration lengths of UV light of more than 100 µm, may exhibit deterioration and mechanical breakdown after being subjected to UV light.) In various embodiments the encapsulant 220 includes or consists essentially of black epoxy resin (i.e., epoxy resin having therewithin one or more pigments to give the resin a black color). In some embodiments, the encapsulant 220 may include a plurality of beads (e.g., glass beads) and/or other fillers therewithin.

As shown in FIG. 2, a shallow portion (or "barrier layer") 225 of the encapsulant 220 immediately surrounding the UV LED chip 205 may be a barrier to UV light, and a remaining portion 230 of the encapsulant 220 farther from the UV LED chip 205 may even be transparent and/or non-UV-resistant, as it will not be subjected to the energetic radiation from the UV LED chip 205. In some embodiments of the invention all of the encapsulant 220 is UV opaque, while in other embodiments of the invention the remaining portion 230 of the encapsulant 220 is substantially UV transparent. The UV-opaque barrier layer 225 may be dispensed and/or molded around the UV LED chip 205 before the remaining encapsulant 220 (i.e., portion 230) is disposed around the barrier layer 225 and the UV LED chip 205. In various embodiments of the invention, with the barrier layer 225 in place, substantially all of the light emitted from the packaged UV LED 200 is emitted through the rigid lens 210 at the top of the package. The barrier layer 225 and the portion 230 of the encapsulant may include, consist essentially of, or consist of different materials, or barrier layer 225 and portion 230 may be composed of one or more of the same materials (such as epoxy, e.g., epoxy resin), with the barrier layer 225 including one or more other components (e.g., pigment) making barrier layer 225 substantially UV opaque.

In various embodiments of the present invention, the encapsulant 220 (e.g., barrier layer 225) vertically overlaps the lens 210 as shown in FIG. 2. In some embodiments, the top surface of the encapsulant 220 (at least the portion of the encapsulant immediately proximate and/or in contact with lens 210) is higher than the bottom surface of lens 210 by a distance of at least 0.02 mm, at least 0.05 mm, or even at least 0.1 mm. This vertical overlap of the encapsulant 220 may advantageously suppress or substantially prevent formation of bubbles within the interface material 215 (or between the interface material 215 and the lens 210 and/or the UV LED chip 205) and/or suppress or substantially prevent partial or full detachment of the lens 210 (and/or at least a portion of the interface material 215) from the UV LED chip 205 during thermal curing of the encapsulant 220 and/or during UV emission (e.g., during operation and/or during burn-in processes in manufacturing). For example, when the encapsulant 220 is cured by e.g., application of heat, at least a portion of the encapsulant 220 may thermally contract (due to, e.g., heat-induced volumetric shrinkage of the encapsulant 220) and thereby apply a downward force (or "down force") on lens 210. The encapsulant 220 may thus include, consist essentially of, or consist of a heat-contractive material, e.g., a resin of polytetrafluoroethylene, polyetheretherketone, a fluoropolymer such as a perfluoroalkoxy alkane, and/or epoxy.

The amount of downward force imposed on lens 210 may be, e.g., more than 0.05 Newtons (N), more than 0.1 N, or even more than 0.2 N. The amount of downward force may be less than or equal to 10 N. The downward force may advantageously force the lens 210 toward the UV LED chip 205, maintaining contact therebetween, and thereby suppress or substantially prevent formation of bubbles at interface material 215. Such bubbles may be due, at least in part, to, e.g., gas generated by decomposition of the interface material 215 during curing and/or during UV emission while the packaged UV LED 200 is in operation. For example, application of heat to an interface material 215 including or consisting essentially of silicone may result in the formation of bubbles of formaldehyde gas. Furthermore, while the packaged UV LED 200 is in operation, the emitted UV light may induce a photochemical reaction that takes place in the interface material 215, and this reaction may result in decomposition of silicone that may result in the formation of bubbles within the interface material 215. The presence of the bubbles may deleteriously impact the UV transparency of the interface material 215, and, if large enough, may result in at least partial detachment of lens 210 from the UV LED chip 205.

Figure 3:
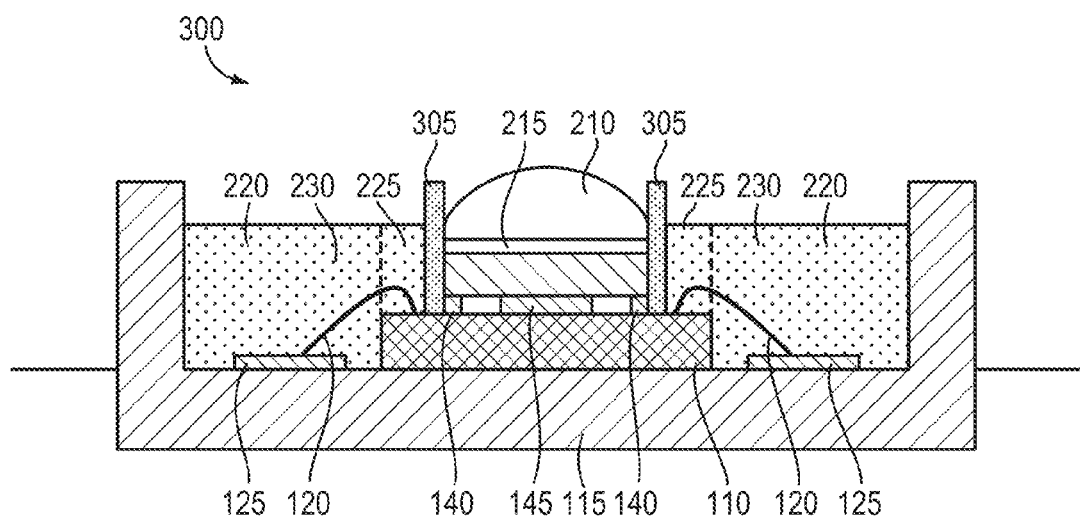
FIG. 3 is a cross-sectional schematic of a packaged UV LED in accordance with various embodiments of the invention.

Referring to FIG. 3, in a packaged UV LED 300, the barrier layer 225 of encapsulant 220 may be augmented or replaced with a non-encapsulant barrier 305 that is substantially opaque to the UV light emitted by the UV LED chip 205. For example, the non-encapsulant barrier 305 may include, consist essentially of, or consist of a UV-reflective metal layer (e.g., aluminum and/or polytetrafluoroethylene (PTFE) or a derivative thereof) disposed around portions of the UV LED chip 205 that would otherwise contact and/or emit light into the surrounding encapsulant 220. The non-encapsulant barrier 305 may be deposited, molded, or otherwise disposed around portions of the UV LED chip 205 that would otherwise contact and/or emit light into the encapsulant 220 and prevents UV light from entering and deteriorating the surrounding encapsulant 220. The non-encapsulant barrier 305 may be a layer or foil deposited or wrapped around the UV LED chip 205 prior to packaging. The non-encapsulant barrier 305 may be attached to one or more portions the package (e.g., the SMD package and/or submount) prior to the UV LED chip 205 being disposed within and electrically and/or mechanically connected to one or more portions of the package. As in FIG. 2, with the non-encapsulant barrier 305 in place, substantially all of the light emitted from the packaged UV LED 300 is emitted through the rigid lens 210 at the top of the package. Although FIG. 3 depicts the barrier layer 225 of the encapsulant 220 present between the non-encapsulant barrier 305 and the remaining portion 230 of the encapsulant 220, in various embodiments of the invention the barrier layer 225 may be omitted (and thus, substantially all of the encapsulant 220 present in packaged UV LED 300 may be substantially UV transparent). In other embodiments, all or a portion of the barrier layer 225 may be disposed between the UV LED chip 205 and the non-encapsulant barrier 305.

EXAMPLE

Figure 4:
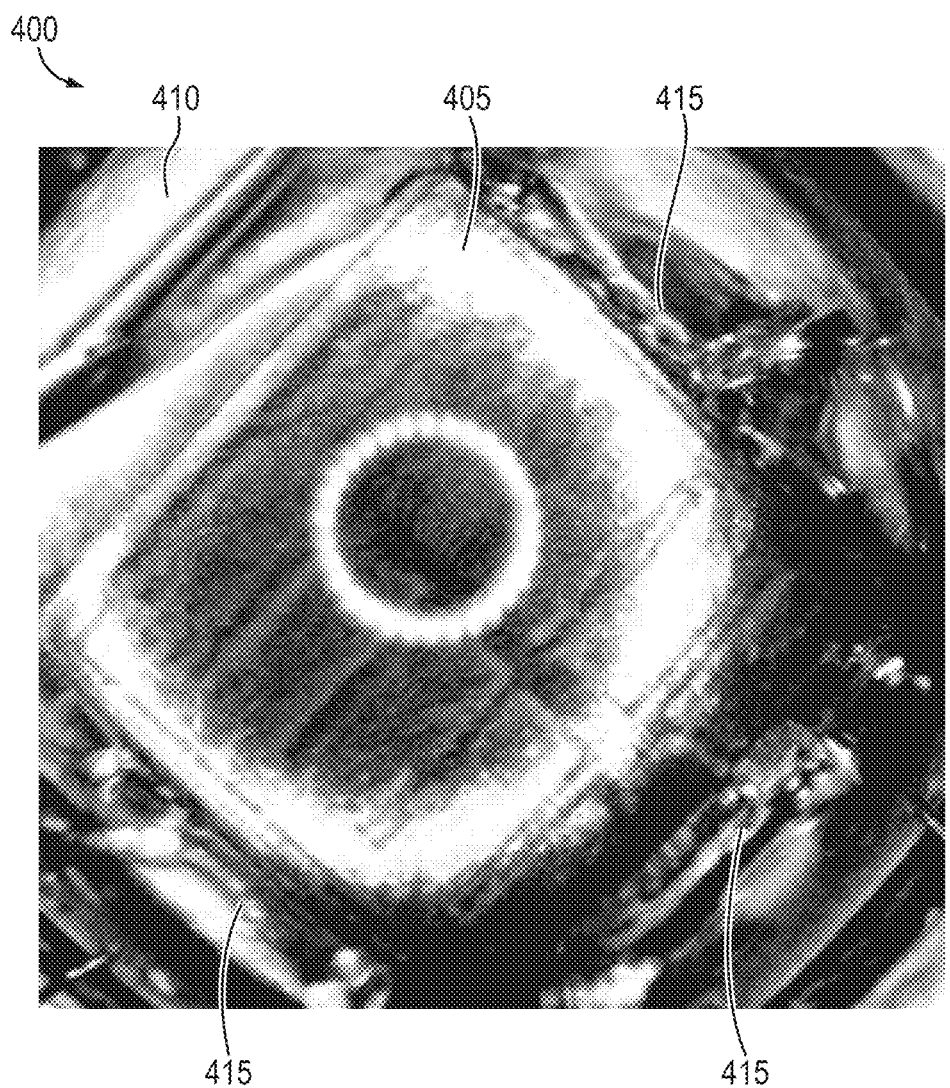
FIG. 4 is a plan-view photograph of a packaged UV LED lacking a UV-blocking barrier between the UV LED chip and a transparent encapsulant after reliability testing.

Reliability testing was performed on 15 packaged UV LEDs, six control devices utilizing transparent encapsulant without a barrier layer, and nine devices utilizing a UV-opaque encapsulant barrier layer 225 in accordance with embodiments of the present invention. The reliability test was performed for a time period of 500 hours, and the devices were exposed to 55° C. and 85% humidity under 150 mA of applied current. Of the six control devices, three (i.e., 50%) of the devices exhibited complete failure, i.e., zero output power due to an open circuit (due to, e.g., broken wire bonds) due to crack formation in the transparent encapsulant. FIG. 4 is a plan-view photograph of a control device 400 without the barrier layer 225 or the non-encapsulant barrier 305 utilized in embodiments of the present invention. As shown, a UV LED chip 405 of the control device 400 is encased in a transparent encapsulant 410, in which cracks 415 have formed after only 255 hours of the reliability testing.

Figure 5:
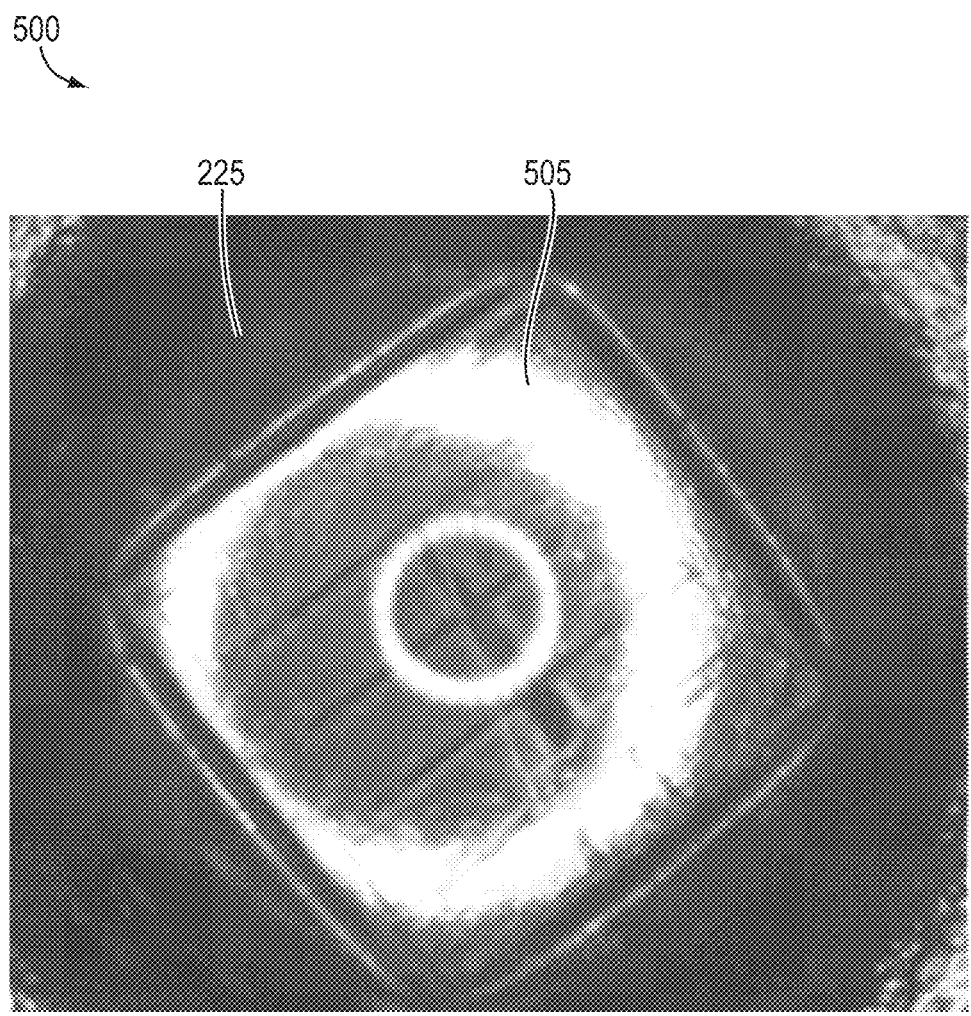
FIG. 5 is a plan-view photograph of a packaged UV LED incorporating a UV-blocking barrier layer in accordance with various embodiments of the invention after reliability testing.

In contrast, all nine of the devices utilizing a UV-opaque encapsulant barrier layer 225 in accordance with embodiments of the present invention maintained more than 50% of their initial output power after the 500 hours of reliability testing, and no cracks or mechanical failures were detected. FIG. 5 is a plan-view photograph of an exemplary packaged UV LED 500 with a barrier layer in accordance with embodiments of the present invention after the reliability testing. As shown, the packaged UV LED 500 of FIG. 5 features a UV LED chip 505 surrounded by a UV-opaque encapsulant barrier layer 225. No cracks in the encapsulant formed for testing times of at least 500 hours.

The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. An illumination device comprising:
a light-emitting device configured to emit ultraviolet (UV) light and having at least two spaced-apart contacts;
a package, wherein (i) at least a portion of the package is disposed beneath the light-emitting device, (ii) the contacts of the light-emitting device are electrically connected to the package, and (iii) the light-emitting device is mechanically attached to a portion of the package;

an encapsulant disposed on the package and at least partially surrounding the light-emitting device; and disposed between the light-emitting device and the encapsulant, a barrier layer configured to substantially prevent UV light emitted by the light-emitting device from entering the encapsulant.

2. The illumination device of claim 1, wherein the barrier layer comprises a second encapsulant disposed adjacent to the light-emitting device.

3. The illumination device of claim 2, wherein the second encapsulant is opaque to UV light emitted by the light-emitting device.

4. The illumination device of claim 3, wherein the encapsulant is substantially transparent to UV light emitted by the light-emitting device.

5. The illumination device of claim 3, wherein the encapsulant is opaque to UV light emitted by the light-emitting device.

6. The illumination device of claim 5, wherein the encapsulant and the second encapsulant comprise the same material.

7. The illumination device of claim 3, wherein a penetration length of UV light within the second encapsulant is less than 25 µm.

8. The illumination device of claim 3, wherein a penetration length of UV light within the second encapsulant is less than 10 µm.

9. The illumination device of claim 1, wherein a penetration length of UV light within the encapsulant is 100 µm or more.

10. The illumination device of claim 1, wherein the barrier layer comprises a material reflective to UV light emitted by the light-emitting device.

11. The illumination device of claim 10, wherein the barrier layer comprises aluminum.

12. The illumination device of claim 10, wherein at least a portion of the encapsulant is substantially transparent to UV light emitted by the light-emitting device.

13. The illumination device of claim 10, wherein at least a portion of the encapsulant is opaque to UV light emitted by the light-emitting device.

14. The illumination device of claim 1, wherein the UV light emitted by the light-emitting device has a wavelength of 265 nm or less.

15. The illumination device of claim 1, wherein the package comprises (i) a submount to which the contacts of the light-emitting device are electrically and mechanically connected, and (ii) disposed below the submount, a surface-mount-device (SMD) package, the submount being electrically connected to the SMD package.

16. The illumination device of claim 15, wherein the submount is electrically connected to the SMD package via one or more wire bonds.

17. The illumination device of claim 1, further comprising a rigid inorganic lens disposed above the light-emitting device and at least partially protruding from the encapsulant.

18. The illumination device of claim 17, wherein the lens comprises at least one of quartz, fused silica, or sapphire.

19. The illumination device of claim 17, wherein a top surface of the encapsulant is disposed above a bottom surface of the lens by at least 0.05 mm.

20. The illumination device of claim 17, wherein at least a portion of the encapsulant applies a downward force on the lens toward the light-emitting device.

21. The illumination device of claim 20, wherein a magnitude of the downward force is greater than 0.1 N.

22. The illumination device of claim 17, further comprising a thin interface material disposed between the lens and the light-emitting device.

23. The illumination device of claim 22, wherein the interface material has a thickness less than 5 µm.

24. The illumination device of claim 22, wherein the interface material comprises silicone.

25. The illumination device of claim 22, wherein at least a portion of the encapsulant applies a downward force on the lens toward the light-emitting device.

26. The illumination device of claim 25, wherein a magnitude of the downward force is greater than 0.1 N.

27. The illumination device of claim 1, wherein the light-emitting device comprises a light-emitting diode.

28. The illumination device of claim 1, wherein the encapsulant comprises a heat-contractive material.

29. The illumination device of claim 1, wherein the encapsulant comprises a resin of at least one of polytetrafluoroethylene, polyetheretherketone, or perfluoroalkoxy alkane.

30. The illumination device of claim 1, wherein the encapsulant comprises epoxy resin.

* * * * *